United States Patent [19]

Poulose et al.

[11] Patent Number: 5,108,457
[45] Date of Patent: Apr. 28, 1992

[54] ENZYMATIC PERACID BLEACHING SYSTEM WITH MODIFIED ENZYME

[75] Inventors: Ayrookaram J. Poulose, San Bruno; Susan A. Anderson, Menlo Park, both of Calif.

[73] Assignee: The Clorox Commpany, Oakland, Calif.

[21] Appl. No.: 286,353

[22] Filed: Dec. 19, 1988

Related U.S. Application Data

[63] Continuation-in-part of Ser. No. 932,717, Nov. 19, 1986, Pat. No. 5,030,240, which is a continuation-in-part of Ser. No. 872,252, Jun. 9, 1986, abandoned.

[51] Int. Cl.$^5$ .................. D06L 3/02; C11D 3/395; C11D 3/386
[52] U.S. Cl. .................. 8/111; 252/95; 252/103; 252/174.12; 435/132; 435/195; 435/198; 935/14
[58] Field of Search .............. 252/95, 186.1, 103, 252/174.12; 435/195–198, 172.3, 874–877, 132; 935/9, 10, 14; 8/111

[56] References Cited

U.S. PATENT DOCUMENTS

| | | | |
|---|---|---|---|
| 3,974,082 | 8/1976 | Weyn | 252/95 |
| 4,385,112 | 5/1983 | Misaki et al. | 435/6 |
| 4,430,433 | 2/1984 | Hammond et al. | 435/228 |
| 4,508,827 | 4/1985 | Olsen | 435/252.34 |
| 4,542,100 | 9/1985 | Hagerorn | 435/253.3 |
| 4,588,688 | 5/1986 | Maxwell | 435/142 |
| 4,707,291 | 11/1987 | Thom et al. | 252/174.12 |

FOREIGN PATENT DOCUMENTS

| | | |
|---|---|---|
| 0130064A1 | 1/1985 | European Pat. Off. |
| 0205208A2 | 12/1986 | European Pat. Off. |
| 0253487A2 | 1/1988 | European Pat. Off. |
| 0253487 | 1/1988 | European Pat. Off. |
| 0260105A2 | 3/1988 | European Pat. Off. |
| 0260105 | 3/1988 | European Pat. Off. |
| 0268452A2 | 5/1988 | European Pat. Off. |
| 0268452 | 5/1988 | European Pat. Off. |
| 0268456A2 | 5/1988 | European Pat. Off. |
| 0268456 | 5/1988 | European Pat. Off. |
| 0272002 | 6/1988 | European Pat. Off. |
| 0341947A1 | 11/1989 | European Pat. Off. |
| 0375102 | 6/1990 | European Pat. Off. |
| WO8809367 | 12/1988 | PCT Int'l Appl. |

OTHER PUBLICATIONS

Wright, C. S. et al., 1969, *Nature*, vol. 221, pp. 235–241.

Kugimiya, W., et al., 1986, "Molecular Cloning and Nucleotide Sequence of the Lipase Gene from *Pseudomonas fragi*". Biochem. Biophys. Res. Comm., vol. 141, pp. 185–190.

Jensen, R. G., 1971 in *Progress The Chem. Fats Other Lipids*, vol. 11, pp. 347–394.

Poulose et al., "Alteration of Substrate Specificity of a Lipase by Site Specific Mutagenesis", *Abstracts of Papers Chemical Congress of North America* (Canada), vol. 3, No. 2, 1988 (Abstract only).

Poulose et al., "Improved Transesterification Through Enzyme Engineering", *Journal of the American Oil Chemists' Society* (U.S.), vol. 64, No. 5, 1987 (Abstract only).

Estell et al., "Engineering of Lipases and Proteases for Improved Transesterification," *Journal of the American Oil Chemists' Society* (U.S.), vol. 64, No. 9, 1987 (Abstract only).

(List continued on next page.)

Primary Examiner—Richard A. Schwartz
Assistant Examiner—Mary E. Mosher
Attorney, Agent, or Firm—Majestic, Parsons, Siebert & Hsue

[57] ABSTRACT

An enzymatic perhydrolysis system, useful for bleaching, has a novel enzyme, a substrate, and a source of hydrogen peroxide, and provides in situ formation of peracid in aqueous solution. The substrate is selected for enzyme catalyzed reaction, and preferably is an acylglycerol with two or three fatty acid chains. The enzyme is hydrolytically and perhydrolytically active even in the presence of anionic surfactants, has lipase activity, and is modified from an enzyme isolatable from *Pseudomonas putida* ATCC 53552.

15 Claims, 1 Drawing Sheet

OTHER PUBLICATIONS

Lewis, "Peracid and Peroxide Oxidations", Chapter 5 in Augustine, Ed., *Oxidation*, vol. 1, pp. 214-258, 1969.

Linden et al., "The Amino Sequence of a Delta[5]-3-Oxosteroid Isomerase from *Pseudomonas putida* Biotype B*", *Journal of Biological Chemistry*, vol. 261, No. 14, pp. 6454-6460, May 14, 1986.

Howe et al., "The Utilization of Tween 80 as Carbon Source by Pseudomonas", *Journal of General Microbiology*, vol. 92, pp. 234-235, 1976.

Shimizu et al., "Production of S-adeosyl-L-homocystein by bacterial cells with a high content of S-adenosylhomocystein hydrolase", *Journal of Biotechnology*, vol. 4, No. 2, pp. 91-100, 1986.

Shimizu et al., "Production of S-adeosyl-L-homocystein by bacterial cells with a high content of S-adenosylhomocystein hydrolase", *Journal of Biotechnology*, vol. 4, No. 2, pp. 91-100, 1986.

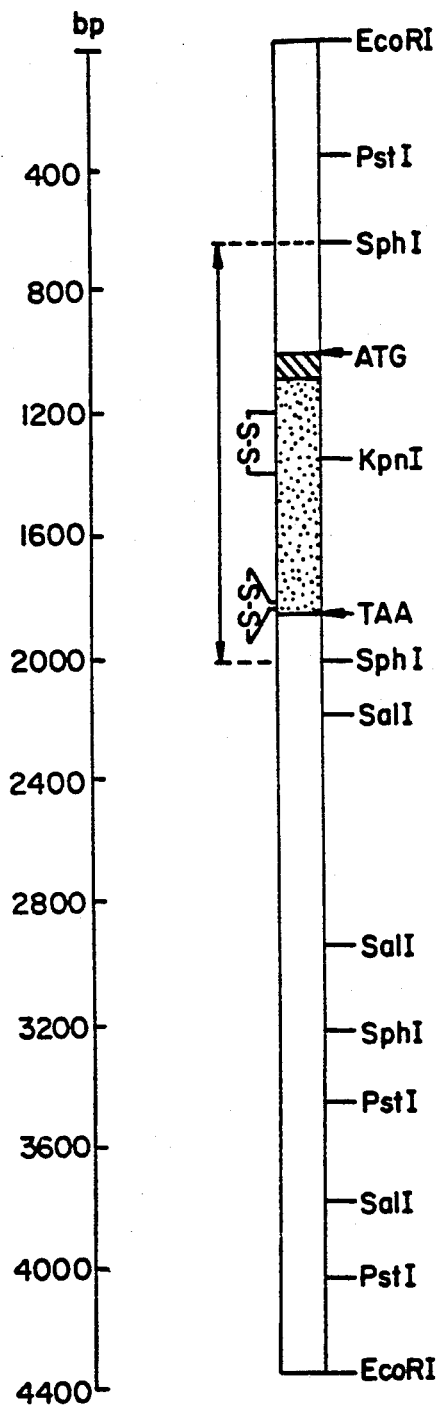
FIG._1.
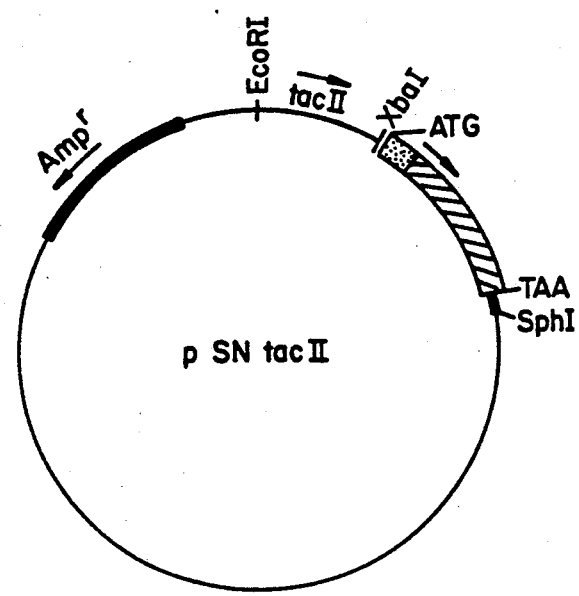
FIG._2.

ENZYMATIC PERACID BLEACHING SYSTEM WITH MODIFIED ENZYME

This is a continuation-in-part of Ser. No. 932,717, filed Nov. 19, 1986, entitled "ENZYMATIC PERACID BLEACHING SYSTEM", U.S. Pat. No. 5,030,240 which is a continuation-in-part of Ser. No. 872,252, filed Jun. 9, 1986, entitled "ENZYMATIC PERHYDROLYSIS SYSTEM AND METHOD OF USE FOR BLEACHING," now abandoned.

FIELD OF THE INVENTION

The present invention generally relates to peracid bleaching, and more particularly relates to a novel enzymatic perhydrolysis system and method of use for the system in aqueous solution for achieving enhanced bleaching.

BACKGROUND OF THE INVENTION

Various bleaches have long been employed in numerous cleaning applications, including the washing and prewashing of fabrics as well as in other applications, such as hard surface cleaning. In these applications, the bleaching agent oxidizes various stains or soils on fabrics, textiles and hard surfaces.

Peroxygen bleaching compounds such as hydrogen peroxide, sodium percarbonate and sodium perborate have been found useful in dry bleach formulations because of their oxidizing power.

It has also been found that addition of certain organic compounds, including activators such as tetracetyl ethylene diamine, to perborate bleaches can improve bleaching performance because of in situ formation of peracids.

Cleaning compositions for fabrics, textiles and other materials including hard surfaces have also been developed which employ various enzymes for removing certain stains or soils. For example, protease enzymes have been found useful for hydrolyzing protein-based stains particularly in the cleaning of fabrics. Amylase enzymes have been found useful against carbohydrate-based stains resulting for example from foods. Lipase enzymes have also been found useful for hydrolyzing fat-based stains in a prewash or presoak mode.

In connection with the use of enzymes in cleaning or detergent compositions, European Patent Application, Publication No. 0 130 064, applied for by Novo Industri A/S, related to improvements in enzymatic additives for use with detergents in washing applications. That publication discussed the use of lipase enzymes for achieving substantially improved lipolytic cleaning efficiency, over a broad range of wash temperatures including relatively low temperatures below 60° C. This reference further disclosed the use of enzymes, including lipases, for direct interaction with stains or soils as a means of at least partially dissolving or loosening such fat-based stains.

Weyn U.S. Pat. No. 3,974,082, issued Aug. 10, 1976, disclosed a bleaching composition and method of use in which an alkyl ester was combined with an esterase or lipase enzyme in an aqueous medium and which was contended to liberate an acyl moiety from the ester. The Weyn patent further contended that the use of this combination together with a percompound would lead to in situ formation of peracid.

Accordingly, there has been found to remain a need for improved bleaching or activated oxidant systems capable of enhanced performance in aqueous solution at low temperature wash conditions while still maintaining high temperature performance.

SUMMARY OF THE INVENTION

The present invention provides an activated oxidant system for achieving enzymatic perhydrolysis of a substrate in the presence of a source of hydrogen peroxide to produce a peracid. Novel enzymes of the invention act catalytically to enhance the reaction of substrates resulting in the in situ formation of peracids. These enzymes have excellent perhydrolysis characteristics and good reactivity for triglyceride substrates, even in the presence of anionic surfactants. Thus, the enzymatic perhydrolysis system of the present invention is compatible with commercially available detergents utilizing anionic surfactants.

Novel enzymes of the invention are modified with respect to a reference enzyme. The reference enzyme is isolatable from *Pseudomonas putida* ATCC 53552, and has the following amino acid sequence:

$^1$ala pro leu pro asp thr pro gly ala $^{10}$pro phe pro ala val ala asn phe asp arg $^{20}$ser gly pro tyr thr the ser ser gln ser $^{30}$glu gly pro ser cys arg ile tyr arg pro $^{40}$arg asp leu gly gln gly gly val arg his $^{50}$pro val ile leu trp gly asn gly thr gly $^{60}$ala gly pro ser thr tyr ala gly leu leu $^{70}$ser his trp ala ser his gly phe val val $^{80}$ala ala ala glu thr ser asn ala gly thr $^{90}$gly arg glu met leu ala cys leu asp tyr $^{100}$leu val arg glu asn asp thr pro tyr gly $^{110}$thr tyr ser gly lys leu asn thr gly arg $^{120}$val gly thr ser gly his ser gln gly gly $^{130}$gly gly ser ile met ala gly gln asp thr $^{140}$arg val arg thr thr ala pro ile gln pro $^{150}$tyr thr leu gly leu gly his asp ser ala $^{160}$ser gln arg arg gln gln gly pro met $^{170}$phe leu met ser gly gly gly asp thr ile ala $^{180}$phe pro tyr leu asn ala gln pro val tyr $^{190}$arg arg ala asn val pro val phe trp gly $^{200}$glu arg arg tyr val ser his phe glu pro $^{210}$val gly ser gly gly ala tyr arg gly pro $^{220}$ser thr ala trp phe arg phe gln leu $^{230}$met asp asp gln asp ala arg ala thr phe tyr $^{240}$gly -continued

```
                              250
ala gln cys ser leu cys thr ser leu leu trp ser val glu arg arg gly leu
```

Modified enzymes of the invention differ from the reference enzyme by at least 1 amino acid occurring either: (1) within about 15 angstroms of serine 126, aspartic acid 176 or histidine 206 (with respect to the tertiary structure of the reference enzyme); or (2) within about 6 amino acids on either side of serine 126, aspartic acid 176 or histidine 206 (with respect to the primary structure of the reference enzyme). The substrate of the activated oxidant system is selected for enzyme catalyzed reaction, in the presence of a source of hydrogen peroxide, to form peracid. Various triglycerides are particularly suitable for forming the substrate. Particularly preferred substrates are trioctanoin and tridecanoin.

The oxidant system of the invention includes a source of hydrogen peroxide which will combine with the substrate, when activated by the enzyme, to produce in situ an organic peracid. For United States laundry conditions, a particularly preferred organic peracid so generated is peroctanoic acid.

The enzymatic perhydrolysis system of the invention provides a number of advantages, including the employment of a relatively inexpensive substrate together with a small amount of an enzyme, for producing the resulting peracid. The preferred triglyceride substrates provide the ability to yield a higher concentration of peracid than provided by equivalent concentrations of a simple ester substrate. The enzymatic perhydrolysis system of the invention has been found to be very effective for producing peracid in low temperature wash solution.

BRIEF DESCRIPTION OF THE DRAWINGS

FIG. 1 is a map of the 4.3 kb EcoRI fragment of a plasmid designated pSNE4. The region crosshatched represents signal peptide codons (codons $-22$ to $+1$) and the stippled region indicates the coding region (codons $+1$ to $+258$) for the mature polypeptide designated Lipase 1. The ATG initiation codon and TAA stop codon are also marked; and FIG. 2 illustrates an *E. coli* expression vector for the Pseudomonas Lipase 1 gene. The stippled region indicates the coding region for the lipase signal sequence of 22 amino acids. The crosshatched region indicates the coding region for the mature lipase protein. Transcription starts at the ATG initiation codon and proceeds in the direction indicated by the arrow to the TAA stop codon. The dark regions on either side indicate the 5'- and 3'-untranslated regions.

DESCRIPTION OF THE PREFERRED EMBODIMENTS

The enzymatic perhydrolysis system of the present invention essentially comprises a novel enzyme as defined below, a substrate, and a source of hydrogen peroxide. Accordingly, the invention is based upon peracid or perhydrolysis chemistry.

In addition to the essential components of the enzymatic perhydrolysis system including novel enzymes, a substrate and a hydrogen peroxide source, the perhydrolysis system of the invention also preferably includes one or more emulsifying agents selected for maintaining the substrate in suspension, or solubilizing, the substrate when in aqueous solution and for promoting interaction of the substrate and enzyme in the presence of hydrogen peroxide from the hydrogen peroxide source. Use of one or more emulsifying agents of this type is particularly contemplated so that the emulsifying agent can assist in forming a liquid phase interface at which the enzyme can better interact with a glyceride substrate. The perhydrolysis system may also preferably include various buffering agents, stabilizers and other adjuncts described in greater detail below.

In order to ensure proper understanding and interpretation of the invention, including the summary and preferred embodiments as well as the claims, some definitions are set forth below to clarify the use of terms employed herein. The defined terms include the following.

"Perhydrolysis" is defined as the reaction of a selected substrate with peroxide to form a peracid and water.

In the preferred perhydrolysis reactions yielding a peracid, both the peroxide starting material and the peracid product are oxidants. Traditionally, inorganic peroxide has been used as the oxidant, for example, in dry laundry bleaches. The peracid product is usually the desired oxidant for laundry bleaches according to the present invention, since the oxidative ability of the peracid product makes it an effective stain removal agent for laundry bleaches, yet the peracid product as oxidant remains sufficiently mild to assure only minimal reaction with dyes and other adjuncts used in laundry bleach products. However, it is within the scope of the present invention that the enzymatic perhydrolysis system be combined with a chemical perhydrolysis system.

"Chemical perhydrolysis" generally includes those perhydrolysis reactions in which an activator or peracid precursor is combined with a source of hydrogen peroxide. A type of peracid precursor for chemical perhydrolysis is disclosed in U.S. Pat. No. 4,735,740, issued Apr. 5, 1988, entitled "DIPEROXYACID PRECURSORS AND METHOD", of common assignment herewith. This application describes sulfonated phenyl esters of dicarboxylic acids which are water soluble and give peroxyacids upon dissolution in water with a source of peroxide by means of in situ chemical perhydrolysis.

"Enzymatic perhydrolysis" is defined as a perhydrolysis reaction which is assisted or catalyzed by an enzyme generally classified as a hydrolase, and more specifically identified below.

Characteristics and preferred examples of the three essential components of the enzymatic perhydrolysis system are first discussed below, followed by a brief discussion of other adjuncts which may be used with the perhydrolysis system and then a number of examples illustrating the enzymatic perhydrolysis system of the invention.

SUBSTRATE

As noted above, the substrate of the enzymatic perhydrolysis system is selected for enzyme catalyzed reaction, in the presence of a source of hydrogen peroxide, to form peracid. As will be discussed in greater detail below, certain substrates are normally present as solids and particularly lend themselves to use in dry formulations including the substrate, enzyme and peroxide source. In such products, it is important that the dry formulation exhibit prolonged shelf life with the enzyme catalyzed reaction not taking place until the formulation is added to an aqueous solution.

For use in a laundry detergent formulation, for example, the substrate may also include surfactant characteristics so that in situ formation of the peracid occurs at or near the surface of the fabric to be cleaned. This assures greater effectiveness of the oxidant responsible for bleaching action.

The substrate of the enzymatic perhydrolysis system may be chosen from a variety of different esters (RCOOR') as the novel enzyme has esterase activity, may be a lipid, as the novel enzyme also has lipase activity, or may be a combination of both (e.g. fatty acid ester lipids). It has been found, in accordance with the present invention, that various fatty acid or glyceride type materials are particularly suitable for forming the substrate of the present enzymatic perhydrolysis system.

Preferably, the substrate of the present invention is a functionalized ester having the structure

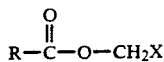

wherein R is a substituent having at least one carbon atom, more preferably where R is a straight chain or branched chain alkyl optionally substituted with one or more functional groups or heteroatoms such as a phenol group, a halogen group or atom, etc. and X is a functional moiety. The substrate is capable of enzymatic hydrolysis as defined above and preferably is ordinarily incapable of substantial chemical perhydrolysis. More preferably, the functional moiety comprises a functionalized polyol or polyether. More broadly, the functional moiety includes at least one carbon atom and at least one functional group.

Even more preferably, the substrate of the invention is selected from the group consisting essentially of:

(i) glycerides having the structure

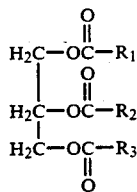

wherein $R_1 = C_1\text{-}C_{12}$, $R_2 = C_1\text{-}C_{12}$ or H and $R_3 = C_1\text{-}C_{12}$ or H;

(ii) an ethylene glycol derivative or ethoxylated ester having the structure

wherein $n = 1\text{-}10$ and $R_1$ is defined above; and (iii) a propylene glycol derivative or propoxylated ester having the structure

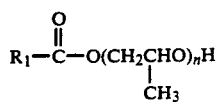

wherein $R_1$ and n are defined as above.

Within the preferred structures referred to immediately above, $R_1$ is more preferably $C_6\text{-}C_{10}$ and most preferably $C_7\text{-}C_9$, $R_2$ is more preferably $C_6\text{-}C_{10}$ or H and most preferably $C_7\text{-}C_9$ or H and $R_3$ is more preferably $C_6\text{-}C_{10}$ or H and most preferably $C_7\text{-}C_9$ or H. In structure (i) above, R, $R_2$ and $R_3$ can be different chain lengths, and mixtures of such different glycerides are suitable in the present invention.

Glycerides undergo hydrolysis when boiled with acids or bases or by the action of lipases. The use of glycerides (that is, acylglycerols), especially diglycerides (diacylglycerols) and triglycerides (triacylglycerols), is particularly preferred within the enzymatic perhydrolysis system of the present invention since each triglyceride molecule is capable of yielding up to three fatty acid or peracid molecules on an equivalence basis. Thus, the use of such a glyceride may be particularly effective in achieving maximum oxidizing power in the presence of a peroxide source and enzyme as discussed in greater detail below.

Broadly, the glyceride substrate is characterized by fatty acid chains including from about 1 to about 18 carbon atoms. Lower molecular weight glycerides derived from such products as acetic acid naturally occur as liquids. Thus, additional processing steps may be necessary in order to include such a substrate in a dry formulation such as laundry detergent. However, the lower molecular weight glyceride products may also tend to be more effective in higher temperature cleaning applications.

High molecular weight glyceride substrates, such as stearic acid characterized by a chain of 17 carbon atoms, normally appear as solids and thus may facilitate their inclusion in a dry detergent formulation, for example. However, such high molecular weight fatty acid chains may not produce maximum oxidizing power in accordance with the present invention.

The most preferred form of substrate for use within the enzymatic perhydrolyis system of the invention has been found to be either trioctanoin or tridecanoin characterized respectively by fatty acid chains (including the carbonyl carbon) of 8 and 10 carbon atoms.

These two triglycerides also tend to be present as solids and thus lend themselves to inclusion in a dry formulation as discussed above. At the same time, trioctanoin and tridecanoin tend to exhibit surfactant characteristics within aqueous solution lending themselves to in situ formation of peracid as discussed above.

All of the substrates discussed above including triglycerides, such as the most preferred trioctanoin and tridecanoin, are relatively inexpensive and are thus also important for reducing initial cost of the enzymatic perhydrolysis system of the present invention. As will also be discussed below, the substrate and hydrogen peroxide source are the two major components of the enzymatic perhydrolysis system in that the enzyme need only be present in very small amounts, less than stoichiometric, to carry out the in situ peracid production contemplated in the aqueous solution. The enzyme thus acts in a catalytic manner in that, while it participates in the reaction, it is not consumed but regenerates itself for further reaction.

PEROXIDE SOURCE

Virtually any source of peroxide is satisfactory as the oxidant source of the enzymatic perhydrolysis system of the invention. For example, the peroxide source may comprise a perborate or percarbonate such as sodium perborate or sodium percarbonate. In addition, the peroxide source may comprise or include hydrogen peroxide adducts such as urea hydrogen peroxide, etc.

Preferred sources of peroxide include sodium perborate monohydrate, sodium perborate tetrahydrate, sodium carbonate peroxyhydrate, sodium pyrophosphate peroxyhydrate, urea peroxyhydrate, sodium peroxide, and mixtures thereof. Sodium perborate monohydrate and sodium perborate tetrahydrate are particularly preferred as alkaline sources of peroxide.

The source of peroxide (that is, compounds yielding hydrogen peroxide in an aqueous solution) itself constitutes a peroxygen bleaching compound. However, the enzymatic perhydrolysis system provides improved bleaching. Accordingly, further discussion of the particular oxidant source is not believed necessary except to the extent that the source is selected to produce hydrogen peroxide also in accordance with the preceding discussion.

ENZYME

A modified enzyme of the invention exists in a hostile, oxidizing environment during use of the enzymatic perhydrolysis system due to the presence of peroxide and the desired peracid. Either peroxide or peracid could inactivate an enzyme in use, so an enzyme suitable for the invention must be sufficiently perhydrolytically active at expected ranges of hydrogen peroxide and at desired ranges of peracid.

Modified enzymes of the invention are modified with respect to a reference enzyme. This reference enzyme is described in U.S. patent application Ser. No. 932,717, filed Nov. 19, 1986. The reference enzyme (sometimes referred to as "Lipase 1") is secreted by and isolatable from a *Pseudomonas putida* strain. Pseudomonas is a genus of short, rod-shaped bacteria. Several strains, including *P. putida,* have been shown to have a limited ability to grow on a minimal media with mono-oleate polyoxyethylene ("Tween 80", available from Atlas Chemical) as carbon source. Howe et al., *J. Gen. Microbiol.,* 92(1), pp. 234-235 (1976). A culture of a novel *Pseudomonas putida* strain from which the Lipase 1 enzyme may be isolated has been deposited in accordance with MPEP 608.1(P) in the permanent culture collection of the American Type Culture Collection, 12301 Parklawn Drive, Rockville, Md. 20852, and has been designated ATCC 53552.

Although the reference enzyme is sometimes referred to as "Lipase 1", it should be understood that the modified enzymes and the reference enzyme can be viewed as lipases or cutinases. This is because analysis of the amino acid sequence for the reference enzyme suggests there are substantial homologies between the nucleotide sequence for this enzyme and the nucleotide sequence of the cutinase gene recently determined for *C. capsici.* Thus, both modified enzymes of this invention and the reference enzyme will sometimes hereinafter be described as glycerol ester hydrolases, or simply as having hydrolase activity.

Modified enzymes of the invention may be obtained as natural or artificial mutants of the *Pseudomonas putida* strain hereinabove described. Further, genetic engineering techniques applicable to lipase production, such as transformation of corresponding genes of the present strain to other cells, may also be applied, and the modified enzymes having hydrolase activity produced by these techniques and then isolated are included in the present invention.

Thus, for example, the reference or modified enzyme may be produced by culturing *E. coli* including the gene for the desired enzyme in a conventional medium for enzyme isolation and purification. Liquid or solid culture can be used. Submerged aeration culture is preferable for industrial production. A conventional nutrient medium can be used.

Culturing temperature may vary depending on the desired rate of growth of the microorganisms and is preferably at 25°-35° C. Culturing time can be selected as desired, and is 15-50 hours. Culturing may be terminated when the highest concentration of enzyme having hydrolase activity is present in the medium.

The desired enzyme is accumulated in the fermentation broth and extraction of the produced enzyme from the broth can be effected as follows:

Cells and cell debris are first removed from the whole cell broth culture by microfiltration and centrifugation, followed by ultrafiltration to concentrate the lipase. Excess salts and color are then removed by dialysis or diafiltration. The crude enzyme solution can then be purified by conventional purification methods for proteins. A powder of the enzyme can be obtained by lyophilization and used in compositions of the invention.

The Lipase 1, or reference enzyme, has the following amino acid sequence:

1                                10
ala pro leu pro asp thr pro gly ala pro phe pro 20
ala val ala asn phe asp arg ser gly pro tyr thr 30
the ser ser gln ser glu gly pro ser cys arg ile 40
tyr arg pro arg asp leu gly gln gly gly val arg 50                             60
his pro val ile leu trp gly. asn gly thr gly ala 70
gly pro ser thr tyr ala gly leu leu ser his trp 80
ala ser his gly phe val val ala ala ala glu thr 90
ser asn ala gly thr gly arg glu met leu ala cys 100
leu asp tyr leu val arg glu asn asp thr pro tyr 110                           120
gly thr tyr ser gly lys leu asn thr gly arg val 130
gly thr ser gly his ser gln gly gly gly gly ser 140
ile met ala gly gln asp thr arg val arg thr thr 150
ala pro ile gln pro tyr thr leu gly leu gly his 160
asp ser ala ser gln arg arg gln gln gly pro met 170                             180
phe leu met ser gly gly gly asp thr ile ala phe 190
pro tyr leu asn ala gln pro val tyr arg arg ala 200
asn val pro val phe trp gly glu arg arg tyr val

```
                        210
ser his phe glu pro val gly ser gly gly ala tyr 220
arg gly pro ser thr ala trp phe arg phe gln leu 230                              240
met asp asp gln asp ala arg ala thr phe tyr gly 250
ala gln cys ser leu cys thr ser leu leu trp ser val glu arg arg gly leu
```

Mutant or variant strains of *Pseudomonas putida* ATCC 53522 may be obtained by environmental selection pressure techniques, by UV irradiation, or by the use of mutagenic chemicals, as will be exemplified hereinafter.

They may also be produced by genetic manipulation techniques, for example by the transfer of plasmid DNA to a multicopy host or by the excision of the chromosomal genes coding for the lipase from the cells of a lipase producing bacteria, followed by the cloning of said genes into a suitable vector molecule. Modified enzymes of the present invention encompass such mutant, variant or cloned strains with retained, altered or enhanced ability to produce the lipase.

FIG. 1 is a map of the 4.3 kb EcoRI fragment of pSNE4. The crosshatched box represents the signal peptide codons (codons −22 to +1), and the stippled region indicates the coding region for the mature Lipase 1 polypeptide codons +1 to +258. The postulated disulfide bonds are shown. The scale is in base pairs (bp). The region sequenced (an SphI fragment of 1363 bp) is indicated with a double arrow. The ATG initiation codon and TAA stop codon are also marked.

The cloning and expression of Lipase 1 illustrated by Example 9 is described herein since a preferred means for carrying out production of the reference enzyme is by cloning, and surprisingly high yields have been obtained by following the Example 9 procedure.

Lipase 1 has excellent hydrolytic activity and produces peracid from the substrate in the presence of a peroxide source, despite the hostile, oxidizing environment. It produces peracid even in the presence of anionic surfactants, which typically inhibit the activity of enzymes. Further, Lipase 1 has a higher ratio of peracid/acid (that is, the reciprocal of the acid/peracid ration also previously discussed) than does a commercially available enzyme such as Lipase CES.

Lipase 1 may be obtained and used as a crude preparation from the fermentation of *P. putida*, but preferably is separated from other proteins and purified by means known to the art, such as by ion exchange and gel permeation chromatography, to yield substantially enzymatically pure Lipase 1. This is primarily because the crude fermentation broth of *P. putida* was found to include another enzyme (hereinafter "Lipase 2") in addition to Lipase 1.

The two enzymes, Lipase 1 and Lipase 2, may be separated by means known to the art such as chromatography. They can be distinguished by their different hydrolysis rates for p-nitrophenyl butyrate and p-nitrophenyl caprylate. Lipase 1 may also be produced by cloning to express this enzyme through a host organism, such as *E. coli*, followed by octyl sepharose chromatography of the cloned Lipase 1, as is more particularly described hereinafter.

Lipase 2 also hydrolyzes glyceride substrates, and may be used in applications such as in fats and oils processing as a digestive aid.

Preferred modified enzymes of the present invention have comparable or improved efficiency in producing peracid than does the reference enzyme. The ratio of acid/peracid (meq/meq) is an indication of the efficiency of the enzyme for producing peracid. Lower ratios usually mean more desirable, high productions of peracid. Enzymes with ratios equal to 1 yield the highest (about 50%) conversion of substrate to peracid within about 14 minutes. As will be more fully illustrated in the examples, Lipase has been experimentally tested with acid/peracid ratios of about 4-5. Preferred modified enzymes in accordance with the invention have been prepared with acid/peracid ratios from about 1 to about 4-5. Particularly preferred modified enzymes have been tested with acid/peracid ratios of 1-3.

These particularly preferred modified enzymes have one or two amino acids that are different from the Lipase 1 enzyme. One particularly preferred embodiment has serine (instead of glutamine) at position 127 and has asparagine (instead of threonine) at position 205. This one particularly preferred embodiment (sometimes designated "Ser-127/Asn-205") maintains a good acid/peracid ratio. Another particularly preferred modified enzyme has asparagine at position 205 and threonine at position 207. This modified enzyme has good specific activity and maintains the acid/peracid ratio. Yet another particularly preferred modified enzyme has asparagine at position 205. This modified enzyme has a good acid/peracid ratio at a low enzyme concentration. Yet another particularly preferred modified enzyme has glutamine at position 205. This modified enzyme gives substantially equivalent yields of peracid as the Lipase 1 type enzyme yet at lower or equivalent enzyme concentrations. Yet other particularly preferred modified enzymes with excellent acid/peracid ratios are: Ser-127/Thr-205, Thr-127/Gln-205, Asn-127/Thr-207, Thr-127/Asn-205, and Arg-127/Ala-207.

As will be seen, these amino acid modifications are all within about 15 angstroms of the normal serine 126, aspartic acid 176 or histidine 206 with respect to the tertiary structure of the reference enzyme. If the crystal structure is not available to determine modifications within the 15 angstrom location, then another way of describing this location in which amino acids of the reference enzyme can be changed is where at least one amino acid change occurs within about six amino acids on either side of serine 126, aspartic acid 176 or histidine 206 with respect to the primary structure of the reference enzyme.

These 3 amino acid positions (126, 176 and 206) of both the reference enzyme and modified enzymes of the invention are believed to be directly involved in amide and ester hydrolysis, and may sometimes be referred to as a "catalytic triad". The catalytic triad may, in fact, be a "catalytic tetrad" because a crystal structure analysis indicates that serine 214 may be within hydrogen bonding distance of aspartic acid 102. As a consequence, modified enzymes of the invention may further differ from the reference enzyme within the "modification zone" on either side of serine 214.

As will be understood, modified enzymes having hydrolase activity and an amino acid sequence substantially corresponding to the reference enzyme, that is Lipase 1, may be obtained and used in a manner analogous to that described for Lipase 1. As a consequence, preparations, purifications and experimental data showing properties of the referene enzyme will now be described, and then will be followed by a description of preparations for modified enzymes in accordance with the invention.

EMULSIFIER

The use of emulsifiers or surfactants is generally desirable as in other peracid bleach products. The use of emulsifiers is believed to be of particular value in establishing and maintaining a phase interface promoting interaction between the enzyme and glyceride substrate. Emulsifiers or surfactants can similarly be of value in establishing and maintaining the enzyme and substrate within the aqueous phase.

Anionic surfactants (generally also present in commercially available detergents) may be employed. Examples of such anionic surfactants include ammonium, substituted ammonium (for example, mono-, di-, and triethanolammonium), alkali metal and alkaline earth metal salts of $C_6-C_{18}$ fatty acids and resin acids, linear and branched alkyl benzene sulfonates, alkyl sulfates, alkyl ether sulfates, alkane sulfonates, olefin sulfonates, hydroxyalkane sulfonates, acyl sarcosinates and acyl N-methyltaurides.

Nonionic surfactants are also suitable for use within the enzyme perhydrolysis system of the invention. Nonionic surfactants include linear ethoxylated alcohols, such as those sold by Shell Chemical Company under the brand name NEODOL. Other nonionic surfactants include various linear ethoxylated alcohols with an average length of from about 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0 to 10 moles of ethylene oxide and about 1 to 10 moles of propylene oxide per mole of alcohol; linear and branched alkylphenoxy (polyethoxy) alcohols, otherwise known as ethoxylated alkylphenols with an average chain length of 8 to 16 carbon atoms and averaging 1.5 to 30 moles of ethylene oxide per mole of alcohol; and mixtures thereof.

Additional nonionic surfactants include certain block copolymers of propylene oxide and ethylene oxide, block polymers propylene oxide and ethylene oxide with propoxylated ethylene diamine, and semi-polar nonionic surfactants such as amine oxides, phosphine oxides, sulfoxides, and their ethoxylated derivatives.

Suitable cationic surfactants include the quaternary ammonium compounds in which typically one of the groups linked to the nitrogen atom is a $C_8-C_{18}$ alkyl group and the other three groups are short chained alkyl groups which may bear inert substituents such as phenol groups.

Further, suitable amphoteric and zwitterionic surfactants, which may contain an anionic water-solubilizing group, a cationic group and a hydrophobic organic group, include amino carboxylic acids and their salts, amino dicarboxylic acids and their salts, alkylbetaines, alkyl aminopropylbetaines, sulfobetaines, alkyl imidazolinium derivatives, certain quaternary ammonium compounds, certain quaternary ammonium compounds and certain tertiary sulfonium compounds. Other examples of potentially suitable zwitterionic surfactants can be found in Jones U.S. Pat. No. 4,005,029, at columns 11-15, which are incorporated herein by reference.

Other exemplary emulsifiers include water soluble or dispersible polymers, such as polyvinyl alcohol (PVA), polyvinylpyrrolidone (PVP), methylhydroxypropylcellulose (MHPC), etc. as well as bile and other natural emulsifiers.

OTHER ADJUNCTS

Additional adjuncts of a wide variety may be considered for use in combination with the enzymatic perhydrolysis system of the present invention, depending upon the specific application contemplated. For example, the enzymatic perhydrolysis system may be employed or included within a wide variety of cleanser applications or formulations such as straight bleach products, prewash products (which are often in liquid form) and even various hard surface cleansers.

For liquid formulations, it may be convenient to keep the hydrogen peroxide source separate from either the substrate or the enzyme, and preferably, from both. This could be accomplished by using a multiple chambered dispenser, such as that disclosed in Beacham et al. U.S. Pat. No. 4,585,150, issued Apr. 29, 1986, and commonly assigned to The Clorox Company.

Suitable adjuncts may include fragrances, dyes, builders, stabilizers, buffers, etc. Stabilizers may be included to achieve a number of purposes. For example, the stabilizers may be directed toward establishing and maintaining effectiveness of the enzyme for original formulation components or even intermediate products existing after the formulation is placed in an aqueous solution. Since enzymes may be hindered in hydrolysis of the substrates because of heavy metals, organic compounds, etc., for example, suitable stabilizers which are generally known in the prior art may be employed to counter such effects and achieve maximum effectiveness of the enzymes within the formulations.

The preferred pH level for aqueous solutions in which the enzymatic perhydrolysis system is dissolved is about 8-11, more preferably about 9-10. Buffering agents can be utilized in the invention to maintain the desired alkaline pH level for the aqueous solutions. Buffering agents generally include all such materials which are well known to those skilled in the detergent art. In particular, buffering agents contemplated for use in the present invention include, but are not limited to, carbonates, phosphates, silicates, borates and hydroxides.

The following experimental methods, materials and results are described for purposes of illustrating the present invention. However, other aspects, advantages and modifications within the scope of the invention will be apparent to those skilled in the art to which the invention pertains.

EXPERIMENTAL

Example 1

(A) Seeding and Fermenting

A seed medium was prepared with 0.6% nutrient broth (Difco) and 1% glucose (pH 6.5). 100 ml of this medium was sterilized in 500 ml fernbach flasks. The flasks were each seeded with a loopful from an overnight culture of *P. putida* ATCC 53552 grown on nutrient agar, and placed on a Newbrunswick shaker at 250 rpm, 37° C. for 12 hours. The incubated 12-hour culture was then seeded at appropriate volumes (1-10% v/v) into a 1 liter fermenter (250 ml working volume), a 15 liter Biolafitte fermenter (12 liters working volume), or a 100 liter Biolafitte fermenter provided with a temperature controller, RPM, airflow and pressure controller. The fermenter medium contained 0.6% nutrient broth (Difco), 0.3% apple cutin, and 0.2% yeast extract (Difco), with an initial pH of 6.5. The medium was adjusted to pH 6.8 and sterilized for 40 minutes before seeding. Bacterial growth and enzyme production were allowed to continue in the fermenter for 12–15 hours.

(B) Enzyme Recovery by Microfiltration

The crude fermentation culture was first filtered in a Amicon unit outfitted with two Romicon microporous membranes (0.22μ) to remove cells. Remaining enzyme in the retentate which was bound to the cutin particles was removed by centrifugation. Total recovery approached 90%.

(C) Concentration and Dialysis of Whole Cell Filtrate

The recovered filtrate from the Amicon unit was concentrated to a volume of 3 liters on an Amicon ultrafiltration unit with two Romicon Pm 10 modules. The concentrated material was then dialised with 20 liters of 0.01M phosphate buffer, pH 7.5, to remove salts and color. Recovery at this stage averaged about 80%. Total activity for this crude preparation was $8.68 \times 10^6$ units A unit of lipase activity is defined as the amount of enzyme which results in an increase of absorbance at 415 nm of 1.0/minute when incubated at 25° C. with 2.0 mM p-nitrophenylbutyrate in 0.1 M pH 8.0 Tris-HCl buffer containing 0.1 wt. % Triton X-100.

Example 2

Lipase Activity After Ultrafiltration and Diafiltration

The binding of three p-nitrophenyl substrates and the turnover kinetics were studied for the crude preparation of Example 1(C), where reaction conditions were 0.1M Tris with 0.1 wt. % Triton X-100, pH 8.0, at 25° C. The substrates were p-nitrophenyl caprylate, p-nitrophenyl laurate, and p-nitrophenyl palmitate, and the data is set out in Table 1.

TABLE 1

| Substrate | $K_m(\mu M)$ | $V_{max}(\mu mole/min/mg\ protein)$ |
| --- | --- | --- |
| PNPC | 214 | 802 |
| PNPL | 167 | 214 |
| PNPP | 183 | 112 |

The Example 1(C) preparation was used in a variety of experiments, further described below, which showed utility with the enzymatic perhydrolysis system of the invention; however, the Example 1(C) preparation includes two enzymes designated "Lipase 1" and "Lipase 2". Lipase 1 is the better perhydrolase, and particularly preferred embodiments of the invention utilize substantially enzymatically pure preparations of Lipase 1. A separation and purification of the crude Example 1(C) preparation is described in Example 3, a complete separation of Lipase 1 and Lipase 2 is described in Example 4 (preferred to obtain substantially enzymatically pure Lipase 1), and an extremely pure sample of Lipase 1 preparation (i.e. analytically pure for sequencing) is described in Example 5.

Example 3

Partial Purification of Lipase 1 and Lipase 2 by Ion Exchange and Gel Permeation Chromatography Lipase 1 was initially partially purified from *Pseudomonas putida* fermentation broth by DEAE Sephacryl chromatography followed by Sephadex G-100 gel permeation chromatography. A DEAE column was equilibrated in 10 mM sodium phosphate buffer, pH 8, and the crude protein was applied to the column in the same buffer. PNB (p-nitrophenyl butyrate) hydrolase activity that was not bound to the column was associated with Lipase 1. Lipase 1 thus obtained from the DEAE step was subjected to chromatography on Sephadex G-100 in 10 mM sodium phosphate buffer pH 8. Lipase 1 eluted from this column as a discrete peak, and was identified by PNB hydrolase activity as well as perhydrolytic activity.

Example 4

Complete Separation of Lipase 1 and Lipase 2 by Hydrophobic Chromatography

Lipase 1 may be separated completely from Lipase 2 by chromatography on hydrophobic resins. The enzyme solution of Example 1(C) after ultrafiltration and diafiltration was adjusted to 0.5M NaCl and applied to a 0.8×7 cm octyl Sepharose column equilibrated in 10 mM Tris(Cl) pH 8, 0.5M NaCl and washed to remove unbound protein. The following washes were then employed: 10 mM Tris(Cl), pH 8, 2M urea; 10 mM Na phosphate pH 8; 10 mM phosphate, pH 8, 0.5M NaCl. After washing, the column was then developed with a linear gradient to 50% n-propanol. The column fractions were then assayed for activity on p-nitrophenyl butyrate (PNB) and p-nitrophenyl caprylate (PNC) in order to locate the lipase activities. Two lipases were clearly resolved, fraction 32 with a PNB/PNC ratio of 4.6 and fraction 51 with a PNB/PNC ratio of 1.40. These have been designated Lipase 1 and Lipase 2, respectively.

The fractions from this column were further analyzed by SDS gel electrophoresis. This analysis revealed that the two lipase activities track with 30,000 molecular weight bands characteristic of procaryotic lipases; in addition, Lipase 2 migrated as a doublet, and was clearly resolved from the single band of Lipase 1. Prior to sequence analysis, these two partially purified enzymes were separated from the high and low molecular weight contaminants by reverse phase chromatography.

Example 5

Purification of Lipase 1 by HPLC in Preparation for Enzyme Peptide Fragmentation Prior to sequence analysis, the partially purified material of Example 3 was further purified by chromatography on a 4.8×100 mm, SynChromPak C4 reverse phase HPLC column. The system was equilibrated in 0.05% triethylamine (TEA) and 0.05% trifluoroacetic acid (TFA) (Solvent A) at 0.5 mL/min. 100 μg to 1 mg of Lipase 1 was injected onto the column and the protein eluted at 0.5 ml/min with a compound gradient of Solvent A and n-propanol containing 0.05% TEA and 0.05% TFA (Solvent B) B/minute. A typical gradient was +5% from 0 to 20%B and then +0.5% B/minute to 60% B. All lipase is inactivated by this HPLC solvent system. The protein peaks eluting at about 35% Solvent B (Lipase 1) or at about 39% Solvent B (Lipase 2) were collected and used for further sequence analysis and preparation of CNBr fragments.

Example 6

Preparation and Purification of Cyanogen Bromide Peptide Fragments for Amino Acid Analysis The cyanogen bromide peptide fragments for amino acid sequence analysis were prepared and purified as follows. An aliquot of pooled Lipase 1 of Example 5 was dried in a SpeedVac centrifuge and then resuspended to 10 mg/ml in 8 M urea, 88% formic acid. The solution was mixed with one volume of 200 mg/ml CNBr in formic acid and incubated in the dark at room temperature for 2hours. The product was then desalted into 40% solvent B:50% solvent A (see above) on a 0.8×7 cm IBF-TrisAcryl GF05 (coarse) column prior to reverse phase analysis. The peptides were initially separated using the same protocol as listed above for the purification of Lipase 1 by reverse phase. Solvent B, however, was changed to 35% propanol:65% acetonitrile (containing TEA and TFA). The initial digest and the peaks after chromatography were also analyzed on SDS/urea/pyridine gels followed by silver staining.

Two peaks were chosen from the chromatogram and subjected to rechromatography employing the conditions dictated above, this time on a 0.48×25 cm SynChromPak C4 column. After rechromatography, the purified peptides were held for sequence analysis.

Example 7

Distinction of Lipase 1 from Lipase 2: Preparation of Cyanogen Bromide Fragments of Lipase 1 and Lipase 2

The purified fractions of Lipase 1 and Lipase 2 from the octyl Sepharose column (as in Example 4) were each diluted with 3 volumes of solvent A (0.05% triethylamine and 0.05% trifluoroacetic acid) and chromatographed (as in Example 5). As described in Example 4, the purified proteins were analyzed by SDS gel electrophoresis, and then pooled individually for comparison of the CNBr fragments and the N-terminal amino acid sequences of Lipase 1 and Lipase 2.

Example 8

Specific Activity of Lipase 1

The specific activity of Lipase 1 was determined using the enzyme purified as in Example 4. Substantially enzymatically pure Lipase 1 has a specific enzyme activity of 3750 units per mg protein as defined in Example 1(C).

Example 9

Preparation of Cloned Lipase 1 in *E. Coli* Cloning of the Lipase 1 Gene of *Pseudomonas Putida*

The *Pseudomonas putida* strain (ATCC 53552) was grown overnight at 37° C. in 200 ml LB (Luria Broth) medium. Cells were harvested by centrifugation and high molecular weight total DNA was prepared exactly according to a standard procedure as outlined by Birnboim et al., *Nucleic Acids Res.* 7, pp. 1513–1523 (1979). The DNA was digested to completion with EcoRI and ligated with T4 DNA ligase to a preparation of plasmid pBR322 (ATCC 37017) digested with EcoRI and dephosphorylated with bacterial alkaline phosphatase. All enzymes used for the manipulation of DNA were used according to the manufacturers' directions (New England Biolabs or Bethesda Research Laboratories). The ligated DNA was used to transform *E. coli* 294 (ATCC 31445) and ampicillin resistant (Ampr) colonies were selected. Accordingly, approximately $2 \times 10^4$ transformants were obtained (approximately $5 \times 10^3$/plate). Plates were flooded with a solution of 4-methylumbelliferylbutyrate (10 mM in 50 mM Tris-HCl, pH 8.0) and then illuminated with an ultraviolet lamp (wavelength 340 nm). Colonies which hydrolyzed the substrate to release the highly fluorogenic compound 4-methylumbelliferone appeared as intensely blue. Using this method 13 positive colonies were obtained. From each of these positive colonies a plasmid miniprep was prepared by the alkaline lysis method as described in Birnboim, supra. Each plasmid was digested with EcoRI and resulting fragments were resolved by polyacrylamide gel electrophoresis as described by Maniatis et al., *Molecular Cloning: A Laboratory Manual*, Cold Spring Harbor Laboratory, Cold Spring, N.Y. (1982). Most plasmids contained a single inserted fragment of 4.3 kb. The others contained other fragments in addition to this fragment. This result suggested that all positive colonies arose as a result of the expression of a common cloned gene contained on the 4.3 kb fragment. One of the plasmids which contained only the 4.3 kb fragment, designated pSNE4, was selected for detailed analysis.

Plasmid pSNE4 was digested with a variety of restriction enzymes which have 6 bp recognition sequences. These enzymes were used singly or in pairs. Analysis of the fragment sizes resulting from these experiments allowed the generation of a preliminary restriction endonuclease cleavage map of the 4.3 kb EcoRI insert of PSNE4. This map is shown in FIG. 1.

Several subfragments of the EcoRI insert of plasmid PSNE4 which were at least 840 bp were subcloned into pBR322 in order to see if any contained a functional gene. Among the plasmids which were found to contain functional lipase genes was pSNES1, which contains a 2.3 kb EcoRI/SalI fragment from the EcoRI insert of pSNE4. (See FIG. 1 for map location of this fragment.)

The inserted fragment of pSNES1 was digested with further restriction enzymes and the resulting small fragments were subcloned into bacteriophage M13 vectors, described by Roberts, *Nucleic Acids Res.*, 12, supplement r167–r204 (1984), for sequencing by the dideoxy chain termination method of Sanger et al., *Proc. Natl. Acad. Sci. USA* 74, pp. 5463–5467 (1977). The sequence of the 1.36 kb of DNA between the SphI sites (refer to FIG. 1), when translated in all possible reading frames, revealed a large open reading frame which includes the NH2-terminal amino acid residues of the protein as determined by direct amino acid sequencing (residues 1–16). This open reading frame also contains the code for two other directly sequenced peptides (residues 94–105 and residues 173–190). The methionine at position −22 is believed to be the initiation codon because it begins the code for a highly hydrophobic region typical of signal peptides. This signal peptide is presumably cleaved off during the secretion process after the alanine at position −1. The open reading frame ends at position 259, indicating that the encoded mature protein has 258 residues.

Regulated Expression of *P. putida* Lipase 1 Gene in *E. coli*

In order to achieve the regulated expression of the *P. putida* lipase gene in *E. coli*, an XbaI site was first introduced just before the ATG initiation codon by site directed mutagenesis, Adelman et al., *DNA* 2, pp. 183–193 (1983) in bacteriophage M13, and the modified gene was subsequently cloned into an expression vector which contains the strong tacII promoter, deBoer et al., *Proc. Natl. Acad. Sci. USA* 80, p. 2125 (1983). This was done by first digesting pSNES1 with SphI.

The 2.4 kb SphI fragment containing the entire lipase coding sequence was isolated and ligated into the replicative form (RF) of M13mp19 at its SphI site and the mixture was used to transfect *E. coli* JM101 (ATCC 33876). Clear plaques were picked and the bacteriophage (template) DNA in which the SphI fragment was present in a counterclockwise orientation was prepared. A partially complementary single-stranded fragment of DNA consisting of 50 nucleotides was synthesized which contained an XbaI site immediately 5o of the Lipase 1 ATG initiation codon. This 50-mer complements the template DNA from the −27 nucleotide position (before the ATG initiation codon) to the −9 position and from the +1 (the A of the ATG) to the +20 position. Between the −9 and the +1 positions, however, the sequence 5'-AACCTTCG-3' of the native lipase promoter region was to be changed to 5'-TATCTAGAATT-3' of the tacII promoter. Mutagenesis was performed.

Three hundred plaques were screened by hybridization with a $^{32}$P-labeled synthetic oligonucleotide (5'-ATGAGGTATCTAGAATTATG-3') which spans the area of change. An RF of a positively hybridizing clone was prepared and cleaved with XbaI and SphI. A 1 kb XbaI/ShpI fragment containing the gene was isolated and ligated into a vector obtained by digesting pHGH907tacII, described by deBoer, supra, with XbaI and SphI and isolating a 4.1 kb XbaI/SphI fragment containing the tacII promoter, and the ampicillin resistance gene. JM101 cells were then transformed with the ligation mixture. An ampicillin resistant colony (containing plasmid pSNtacII--see FIG. 2) was selected.

To determine the levels of cloned Lipase 1 synthesized by *E. coli*, JM101/pSNtacII was grown in 20 mls LB medium supplement with 1 mM isopropyl-B-D-thiogalactoside (IPTG) for 10h at 37° C. 294/pBR322 was used as a negative control. The cells were separated from the culture supernatant by centrifugation and then fractionated into periplasmic and membrane/cytoplasmic components, Koshland, supra. Each fraction was tested for activity by p-nitrophenylbutyrate hydrolysis. β-lactamase (periplasmic marker) and β-galactosidase (cytoplasmic marker) were also measured, Gray et al., *Proc. Natl. Acad. Sci. USA* 81, pp. 2645-2649 (1984), in order to confirm the effectiveness of the cell fractionation procedure. Most of the Lipase 1 activity (74%) was present in the culture supernatant. Most of the cell associated enzyme was found in the cell wash fraction (17% of the total) with smaller amounts present in the periplasmic (2%) and cytoplasm/membrane (7%) fractions. No Lipase 1 activity was present in any fractions of the 294/pBR322 negative control culture.

Broth from the fermentation of *E. coli* strain JM101 harboring the plasmid pSNtacII was adjusted to 0.5M NaCl and purified by octyl Sepharose substantially as described when *P. putida* is fermented (Example 4), except the propanol gradient was eliminated and elution was achieved with 20% acetonitrile in 10 mM Na phosphate, pH 8, 0.5M NaCl. The isolated product (cloned from the gene expressing the enzyme) was analyzed by SDS gels and migrated identically to the Lipase 1 product isolated from the original *Pseudomonas putida* strain.

Example 10

Preparation of Cyanogen Bromide Fragments from Cloned Lipase 1

Cyanogen bromide fragments from cloned Lipase 1 were prepared as follows. The product from the octyl Sepharose purification of cloned product (Example 9) was diluted with 3 volumes of solvent A and purified on the short C4 HPLC column, as described for Lipase 1 and Lipase 2 isolated from *Pseudomonas putida*. The product was analyzed on SDS gel.

Example 11

Comparison of CNBr Fragments of Lipase 1 from *P. putida* and CNBr Fragments from the Cloned Lipase 1 in *E. coli*

CNBr fragments of Lipase 1 from *P. putida* and CNBr fragments from the cloned Lipase 1 in *E. coli* were compared. HPLC purified Lipase 1 and 2 from Pseudomonas and the cloned Lipase 1 were each hydrolyzed by CNBr as described in Example 6 above. The products were analyzed by SDS/urea/pyridine electrophoresis. The results indicate the cloned protein is clearly Lipase 1. Lipase 1 isolated from *P. putida* (as in Examples 4-5) was shown to be identical to the cloned Lipase 1 isolated from *E. coli* by the following criteria: (a) Lipase 1 from either organism was isolated by the same chromatographic procedure (as in Example 4); (b) the amino acid sequences of the N-terminal of the Lipase 1 isolated from either organism were the same; (c) the CNBr fragment pattern showed that the Lipase 1 and Lipase 2 are clearly distinguished and that the CNBr fragments of Lipase 1 from either *P. putida* or *E. coli* are identical; (d) the p-nitrophenyl butyrate and p-nitrophenylcaprylate substrate activity ratio of Lipase 1 from both bacterial sources is the same; and (e) the hydrolysis/perhydrolysis ratio with tricaprylin as substrate is the same for Lipase 1 as isolated from both organisms.

Example 12

Assay for Peracid Generation

An assay was developed for determining peracid generation by monitoring the oxidation of o-phenylene diamine ("OPD"). The oxidation of OPD by peracid is much quicker than by $H_2O_2$, and results in an absorbance increase at 458 nm. The assay procedure was to withdraw 0.1 ml of the reaction mixture being tested, to add 0.2 ml OPD solution (although in some instances, the OPD was added to the initial reaction mixture), incubate at room temperature for 5 minutes, add 0.9 ml CHCl3/CH3OH (1/1 v/v), centrifuge 1 minute, and read the absorbance at 458 nm. The standard plot (for C8 peracid) was linear up to at least 36 ppm peracid.

Example 13 illustrates that a "crude" preparation including the preferred enzyme ("Lipase 1") and the other, but less preferred enzyme ("Lipase 2"), has acceptable hydrolytic activity in the presence of either 30 ppm peroctanoic acid or up to 800 ppm hydrogen peroxide.

Example 13

Stability of Lipase in the Presence of Hydrogen Peroxide and Peracid

A quantity of the Example 1 enzyme preparation (including a mixture of Lipase 1 and Lipase 2, as in Example 1(C)), 1 mg/ml, was combined with 0.5 wt. % trioctanoin, 100 mM NaCl, and 10 mM sodium phosphate to form a 2 ml reaction volume with pH 10 for each of five samples. The reaction mixture for each sample was maintained at 30° C. The five samples were tested for hydrolytic activity as follows. One sample had 30 ppm of peroctanoic acid added and the hydrolytic activity of the enzyme was determined ($\mu$mole NaOH/min), as was that of a control (with no peroctanoic acid added). Two other samples had hydrogen peroxide added (400 ppm and 800 ppm, respectively) and the hydrolytic activity determined ($\mu$mole NaOH/min) as was that of a control. Table 2 sets out the data.

TABLE 2

| Sample | Added | Hydrolytic Activity ($\mu$mole NaOH/min) |
| --- | --- | --- |
| 1 | (Control) 0 ppm peroctanoic acid | 0.48 |
| 2 | 30 ppm peroctanic acid | 0.242 |
| 3 | (Control) 0 ppm hydrogen peroxide | 0.51 |
| 4 | 400 ppm $H_2O_2$ | 0.413 |
| 5 | 800 ppm $H_2O_2$ | 0.379 |

As illustrated by Table 2, the hydrolytic activity of this crude enzyme preparation was reduced by the presence of peroctanoic acid and by hydrogen peroxide; however, the enzyme preparation was considered to be sufficiently hydrolytically active despite the hostile, oxidizing environment.

In a similar manner, the same quantity of a commercially available enzyme (K-30) was tested by adding 400 ppm or 800 ppm hydrogen peroxide to reaction volumes of 2 ml, each with 0.5 wt. % trioctanoin, 100 mM NaCl, and 10 mM sodium phosphate. The hydrolytic activity was determined ($\mu$mole NaOH/min), as was that of a control. Table 3 sets out the data for comparison with Table 2.

TABLE 3

| Sample | Added | Hydrolytic Activity ($\mu$mole NaOH/min) |
| --- | --- | --- |
| 6 | (control) 0 ppm $H_2O_2$ | 0.223 |
| 7 | 400 ppm $H_2O_2$ | 0.135 |
| 8 | 800 ppm $H_2O_2$ | 0.056 |

Comparison of the Tables 2 and 3 data shows that the inventive enzyme is considerably more stable (less sensitive) in the presence of an oxidizing environment than the previously known enzyme.

Example 14A illustrates that a substantially pure preparation of the preferred enzyme (Lipase 1) is not inactivated, and has excellent hydrolytic activity, in the presence of 400 ppm hydrogen peroxide and 4-7 ppm peroctanoic acid generated from the perhydrolysis of trioctanoin. Example 14B illustrates the effect of pH on the perhydrolysis to hydrolysis ratio.

Example 14A

Stability of Lipase 1

Another enzyme preparation as in Example 4 (substantially pure Lipase 1) was tested in both the presence and the absence of hydrogen peroxide. The hydrolysis rate was measured as $\mu$moles/ml/10 min. Each sample had substrate of 1.0 wt. % trioctanoin emulsified with 0.1 wt. % sodium dodecyl sulfate ("SDS"), and o-phenylenediamine (OPD) at 4 mg/ml. The reaction volume for each sample was 2 ml, and the temperature was 27° C. The substantially pure Lipase 1 preparation did not experience any inactivation by the presence of hydrogen peroxide at 400 ppm or from the presence of peracid which was generated due to perhydrolysis.

Example 14B

Effect of pH

An enzyme preparation as in Example 4 was tested under the following constant reaction conditions: 1 wt. % trioctanoin in 0.1 wt. % SDS, 380 ppm $H_2O_2$, 1 $\mu$g/ml enzyme, 2 mg/ml OPD, with a reaction volume of 5 ml at 27° C. Each reaction volume had the pH adjusted to a value between 8 and 11, and the perhydrolysis and hydrolysis values determined as $\mu$mole/ml/5 minutes. The optimum pH appears to be about pH 10.

Example 15 shows that the novel enzyme has greater enzymatic reactivity to a lipid than it does to an ester.

Example 15

Peracid Generation from Various Substrates

Each sample had 380 ppm $H_2O_2$, OPD of 2 mg/ml, 1 $\mu$g/ml enzyme (including a mixture of Lipase 1 and Lipase 2, prepared as in Example 1), 1 wt. % substrate (as an emulsion with SDS in a substrate/SDS ratio of 10:1) in 40 mM sodium phosphate buffer. The pH was 9.0 (pH stat), the temperature 27° C., and the reaction volume was 5 ml. Table 4 illustrates the data as $\mu$mole/ml/10 min.

TABLE 4

| Substrate | Hydrolysis (Acid Production) | Perhydrolysis (Peracid Production) |
| --- | --- | --- |
| trioctanoin | 4.24 | 0.42 |
| methyl octanoate | 0.66 | 0.11 |

As illustrated by the data, the novel enzyme has increased reactivity to the triglyceride substrate (with respect to the simple ester), and is shown to be a lipase.

Many commercially available enzymes are inhibited by the presence of anionic surfactant. Indeed, an anionic surfactant such as SDS is routinely used to solubilize proteins in procedures as SDS electrophoresis by binding to the protein molecules, converting them to rodlike shapes, and masking their native charge with the SDS negative charge. Since many, if not most, commercially available detergents include anionic surfactants, the ability of an enzyme to maintain its hydrolytic activity despite the presence of an anionic surfactant is an important advantage.

Example 16 illustrates the retention of hydrolytic activity by an enzyme in accordance with the invention in the presence of anionic surfactant, and the inhibition of activity by a commercially available enzyme for comparison.

Example 16

Comparison of Activities of Lipase 1 and Lipase K-30 in the Presence of Anionic Surfactants Samples were prepared having the same composition and/or reaction conditions except for the particular enzyme. Comparison samples were prepared with the commercially available enzyme Lipase K-30, said to be obtained from Aspergillus niqer, available from Amano, at 8.7 $\mu$g/ml. The inventive enzyme preparation was as in Example 1 at 16.8 μg/ml (to approximate the hydrolysis rate of Lipase K-30). Each sample had trioctanoin as an emulsion with SDS in a weight ratio of 10:1. Sodium phosphate buffer (10 mM) was present, the pH was 10, the temperature was 25° C., and the reaction volume for each same was 2 ml. The data showing trioctanoin hydrolysis for each enzyme in the presence of SDS is set out in Table 5.

TABLE 5

| Amounts of Substrate (wt. %) | Substrate Hydrolysis (μl 0.1N NaOH/min) |
|---|---|
| With Inventive Enzyme: | |
| 0.01 | 2 |
| 0.05 | 7 |
| 0.1 | 11 |
| 0.5 | 13 |
| 1.0 | 12 |
| With Commercially Available Enzyme: | |
| 0.01 | 1 |
| 0.05 | 7 |
| 0.1 | 7.5 |
| 0.5 | 3 |
| 1.0 | 1.5 |

As can be seen by the data of Table 5, the two different enzymes provide about comparable hydrolysis at 0.05 wt. % substrate, but the commercially available enzyme was inhibited by the increasing amount of SDS when the substrate amount increased beyond about 0.1 wt. % trioctanoin. That is, the perhydrolysis rate was relatively poor for Lipase K-30. By contrast, the inventive enzyme was substantially unaffected by the presence of the anionic surfactant.

In tests analogous to Example 16, but with emulsifier (polyvinyl alcohol), both the commercially available Lipase K-30 and the inventive enzyme exhibited good hydrolytic rates.

Example 17

Comparative Enzymatic Peracid Generation

Peracid generation was determined for an enzyme preparation as in Example 3, and compared with the peracid generation of two commercially available enzymes in the presence of 0.5 wt. % SDS. Each test sample had 480 ppm hydrogen peroxide, enzyme at 6μg/ml, trioctanoin substrate at 5 wt. % and 0.5 wt. % SDS. The constant pH was 10 and the temperature was 25° C. Table 6 sets out the perhydrolysis profile of the inventive enzyme.

TABLE 6

| time (min) | peracid generated (ppm) |
|---|---|
| 2 | 3.9 |
| 4 | 7.2 |
| 6 | 8.1 |
| 8 | 9.0 |
| 10 | 9.9 |

By contrast, the amount of peracid generated with commercially available Lipase CES (said to be derived from *Pseudomonas fl.*, available from Amano) remained substantially constant and low (about 0.5 ppm peracid), while the amount of peracid with commercially available Lipase K remains substantially constant and even lower (about 0.3 ppm peracid).

The ratio of perhydrolysis to hydrolysis is very important. One wishes the highest possible conversion to peracid from substrate. The inventive enzyme has a higher ratio of peracid/acid than a commercially available enzyme such as Lipase CES. This means the inventive enzyme more efficiently utilizes its substrate for peracid generation and thus less of the substrate need be present in bleaching formulations.

Example 18

Comparison of Perhydrolysis and Hydrolysis Activities of Lipase 1 and Currently Available Commercial Lipase Perhydrolysis and hydrolysis were measured in samples containing 400 ppm hydrogen peroxide, 0.12M $HPO_4^{-2}$, pH 10.0, and at various concentrations of either a commercially available lipase (CES from Amano) or the inventive enzyme (from Example 1(C) preparation). Perhydrolysis was measured by thiosulfate titration at 14 min. of reaction. Hydrolysis was measured simultaneously by continuous titration using the pH stat. The quantity of substrate was 12.5 wt. % trioctanoin with 0.75 wt. % PVA. The inventive enzyme provided more peracid for a lower substrate hydrolysis, which showed it more efficiently utilized the substrate than did the Lipase CES.

The crude preparation illustrated by Example 1(C) has been discovered to include two enzymes designated "Lipase 1" and "Lipase 2". The perhydrolysis to hydrolysis ratio of one with respect to the other for trioctanoin substrate is different, and Lipase 1 is the better perhydrolase when compared to Lipase 2. Example 19 illustrates these ratios.

Example 19

Effect of Surfactants on the Hydrolytic and Perhydrolytic Activities of Lipase 1 and Lipase 2

Four samples were prepared, and each contained 1 wt. % substrate, 0.1 wt. % surfactant (either SDS or PVA), 400 ppm $H_2O_2$, and 4 mg/ml OPD. The reaction volumes were 2 ml, pH 9.0, and temperature 27° C. Either Lipase 1 (from Example 3 preparation or from Example 9 preparation) or Lipase 2 (from Example 4) was added to the samples. Table 7 sets out the data.

TABLE 7

| Surfactant | Lipase 1 (p-nitrophenyl butyrate hydrolysis units) | Lipase 2 (p-nitrophenyl butyrate hydrolysis units) | Perhydrolysis to Hydrolysis Ratio |
|---|---|---|---|
| SDS | 4 | 0 | 0.19 |
| PVA | 4 | 0 | 0.14 |
| SDS | 0 | 20 | 0.010 |
| PVA | 0 | 20 | 0.011 |
| SDS | 12 | 0 | 0.12 |
| PVA | 12 | 0 | 0.076 |

As may be seen from the Table 7 data, Lipase 1 is a significantly better perhydrolase for trioctanoin substrate than Lipase 2 in the presence of the anionic surfactant, and is an about comparable perhydrolase in the presence of the nonionic surfactant.

Example 20 illustrates that excess of the novel enzyme appears to provide increased hydrolysis, but with no increase in peracid. Again, this shows an effective utilization of substrate.

Example 20

Effect of Enzyme Concentration Upon the Perhydrolysis/Hydrolysis Ratio

The substrate was 1 wt. % trioctanoin emulsified with 0.1 wt. % SDS, there was 400 ppm hydrogen peroxide, 4 mg/ml OPD, a pH of 9.0, a temperature of 25° C., and a reaction volume of 5 ml. Three different amounts of enzyme (prepared as in Example 4) were utilized, with the results illustrated in Table 8.

TABLE 8

| Enzyme Level (PNB* units/ml) | 5 min | 10 min |
|---|---|---|
| | Hydrolysis (μmole/ml) | |
| 3 | 1.7 | 3.2 |
| 6 | 3.5 | 5.9 |
| 12 | 6.1 | 10.1 |
| | Perhydrolysis (μmole/ml) | |
| 3 | 0.42 | 0.54 |
| 6 | 0.51 | 0.78 |
| 12 | 0.57 | 0.87 |

*p-nitrophenyl butyrate hydrolysis

Thus, the perhydrolysis to hydrolysis ratios after 5 minutes were 0.25, 0.15 and 0.09, respectively, and after 10 minutes were 0.17, 0.13 and 0.09, respectively. The smaller amount of enzyme was thus more efficient.

When separated, Lipase 1 and Lipase 2 were found to have quite different hydrolysis rates (hydrolytic activity) for p-nitrophenyl butyrate and for p-nitrophenyl caprylate. Thus, the two novel enzymes can be distinguished by their ratios of p-nitrophenyl butyrate to p-nitrophenyl caprylate hydrolysis, as illustrated by Example 21.

Example 21

Hydrolysis Rates of Lipase 1 and Lipase 2 with p-Nitrophenyl Butyrate and p-Nitrophenyl Caprylate as Substrates The reactions were performed in samples containing 0.1M Tris HCl, pH 8.0 with 0.1 wt. % Triton X-100 nonionic surfactant (available from Rohm & Haas) at 25° C. The hydrolysis rates of 2.0 mM p-nitrophenyl butyrate (PNB) for Lipase 1 (as from Example 3), was 0.60 ( OD 415 nm/min.), while that of 2.0 mM p-nitrophenyl caprylate (PNC) was 0.09, for a PNB/PNC ratio of 7. By contrast, the hydrolysis rate of PNB for Lipase 2 at the same concentration was 0.54, of PNC at the same concentration was 0.44, for a PNB/PNC ratio of 1.

The reference enzyme has been shown to produce peracid in the presence of a broad range of surfactants even under hostile conditions for commercially available enzymes, such as the presence of anionic surfactants.

Example 22

Perhydrolysis Activity of Lipase 1 and With Two Commercially Available Lipases

Samples including either the reference enzyme (as in Example 1(C)), commercially available Lipase K or commercially available Lipase CES were dissolved in an aqueous solution containing a substrate (trioctanoin), hydrogen peroxide, and a mixture of surfactants (anionic and nonionic). The solutions were at room temperature and had a pH of 10.0. Perhydrolysis was calculated as ppm after 14 minutes, as set out in Table 9.

TABLE 9

| Enzyme (1 mg/ml) | Detergent* (% w/w) | Trioctanoin:Emulsifier (% w/w) | $H_2O_2$ (ppm) | Pedrolysis (ppm) |
|---|---|---|---|---|
| Reference enzyme | 0.028 | 9.5:0 | 400 | 4.0 |
| Reference enzyme | 0.026 | 9.5:0.05 (sodium deoxycholate) | 400 | 3.8 |
| Reference enzyme | 0.028 | 9.5:0.15 (sodium deoxycholate) | 381 | 3.4 |
| Reference enzyme | 0.028 | 9.5:0.01 (sodium lauryl sulfonate) | 397 | 3.3 |
| Lipase K | 0.028 | 9.5:0 | 505 | 0 |
| Lipase CES | 0.028 | 9.5:0 | 400 | 0 |
| Lipase CES | 0.026 | 9.5:6.9 (propylene glycol) | 417 | 0 |

*45.1 wt. % CALSOFT F-90 (alkylbenzene sulfonate, available from Pilot Chemical Co.). 40.8 wt. % SLS (sodium lauryl sulfate) and 14.1 wt. % NEODOL 25-7 (C12-C15 alcohol with an aveage ethoxylation of 7, available from Shell Chemical)

The reference enzyme is thus shown to provide strikingly better perhydrolysis in the presence of detergents including anionic surfactants.

The preceding examples are based on the use of a triglyceride substrate with the function group (i) of the preferred substrates referred to above. Other glycerides included within that same functional group could be substituted for the triglyceride in the preceding examples. At the same time, additional substrates as defined above, particularly those included within the preferred functional groups of ethoxylated ester (ii) and propoxylated esters (iii) could be substituted for the triglyceride substrates in the preceding examples.

Further in connection with the preferred functional substrate groups (i), (ii) and (iii) referred to above, specific substrate examples within the first functional group are clearly apparent from the preceding examples.

Examples of substrates from the other two groups are demonstrated by the method of synthesis for a propoxylated ester set forth in Example 23.

EXAMPLE 23

The procedure for preparation of a propylene glycol monoester of carboxylic acid includes the following steps:

(1) Salt Formation and Dehydration: One equivalent of carboxylic acid and 0.09 equivalents of sodium carbonate were combined in a round bottom flask equipped with a magnetic stir bar and an oil bath for heating. The slurry was heated under vacuum to 150° C. with constant stirring for about one hour to achieve dehydration. The vacuum was released and the reaction cooled to room temperature.

(2) Esterification: The cooled acid/acid salt solution from step (1) was combined with about six equivalents of propylene oxide and heated on a warm oil bath at about 60° C. under reflux for approximately eight hours to complete the esterification reaction. (Completion of the esterification reaction was confirmed by G. monitoring).

(3) The reflux condensate was removed and excess propylene oxide boiled off. About 200 milliliters of diethyl ether per 100 millimoles of acid were added and the resulting solution extracted in a separatory funnel with two volumes of 5% sodium carbonate. One volume of brine was then added. The ether layer was dried over sodium sulfate, filtered and rotary evaporated to produce the resulting ester product (typically about 90% pure).

Other examples of functionalized substrates according to functional substrate groups (ii) and (iii) can be produced by similar procedures.

Example 24 illustrates stain removal studies of several preferred formulations.

EXAMPLE 24

Diagnostic evaluations of oxidant performance were performed with 100% cotton swatches stained with crystal violet as follows. Crystal violet (0.125 g) was added to 1.25 liters of distilled water. One hundred two-inch by two-inch undyed, 100% cotton swatches were added to the solution and agitated for eight hours. The cotton swatches (now dyed with crystal violet) were removed from the staining solution and rinsed repeatedly with cold tap water until the effluent was nearly clear. The stained swatches were then individually placed on aluminum foil, blotted with paper towels, and allowed to air dry.

Three preferred formulations including the reference enzyme were prepared, as were corresponding control compositions. The three reference enzyme compositions and the three corresponding control compositions were each used to wash the stained cotton swatches and the stain removal performance evaluated for each. The performance results are summarized in Table 10.

TABLE 10

|  | % Stain Removal |
|---|---|
| Reference Enzyme Composition (a) | |
| 0.06 wt. % trioctanoin | 63.6 |
| 0.04 wt. % sodium dodecylsulfate | |
| 100 ppm H$_2$O$_2$ | |
| 1 µg/ml Lipase 1 | |
| 20 µM EDTA | |
| (pH = 10.5) | |
| Control Composition (a) | |
| 0.06 wt. % trioctanoin | 50.6 |
| 0.04 wt. % sodium dodecylsulfate | |
| 100 ppm H$_2$O$_2$ | |
| 20 µM EDTA | |
| (pH = 10.5) | |
| Reference Enzyme Composition (b) | |
| 0.06 wt. % trioctanoin | 80.4 |
| 0.04 wt. % sodium dodecylsulfate | |
| 200 ppm H$_2$O$_2$ | |
| 1 µg/ml Lipase 1 | |
| 20 µM EDTA | |
| (pH = 10.5) | |
| Control Composition (b) | |
| 0.06 wt. % trioctanoin | 69.8 |
| 0.04 wt. % sodium dodecylsulfate | |
| 200 ppm HO$_2$ | |
| 20 µM EDTA | |
| (pH = 10.5) | |
| Reference Enzyme Composition (c) | |
| 0.02 wt. % trioctanoin | 67.4 |
| 0.02 wt. % sodium dodecylsulfate | |
| 50 ppm H$_2$O$_2$ | |
| 5 µg/ml Lipase 1 | |
| 20 µM EDTA | |
| (pH = 10.5) | |

TABLE 10-continued

|  | % Stain Removal |
|---|---|
| Control Composition (c) | |
| 0.02 wt. % trioctanoin | 52.2 |
| 0.02 wt. % sodium dodecylsulfate | |
| 50 ppm H$_2$O$_2$ | |
| 20 µM EDTA | |
| (pH = 10.5) | |

As may be seen from the data of Table 10, the compositions including reference enzyme provided improved stain removal benefits with respect to the control compositions even though the control compositions included the hydrogen peroxide component. These improved stain removals are due to the enzymatic perhydrolysis system and are particularly striking as occurring in the presence of anionic surfactant which inhibits many prior known commercially available enzymes.

Perhydrolysis or activated oxidant systems disclosed by various of the preceding examples can be used in combination with any of a wide variety of detergent formulations typically employed in cleaning fabrics. Thus, a typical heavy-duty built powdered detergent for U.S. laundry applications includes anionic and/or non-ionic surfactants, phosphate or non-phosphate builders, buffering agents, and miscellaneous additives such as brighteners, perfume, proteases, and the like. The perhydrolysis system of the present invention may be used by itself or as a minor part of such a typical powdered detergent.

Typical heavy-duty built powdered detergents for European conditions have about the same nominal compositions as the U.S. counterparts, but product use concentrations are usually as 1.2% solutions in the washing machines (rather than the about 0.15% solutions typical in United States practice). A preferred formulation for the inventive perhydrolysis system packaged in combination with a typical detergent formulation is from about 3–30 wt. % source of peroxygen, about 0.6 to about 12 wt. % substrate, and about 0.001 to about 0.7 wt. % modified enzyme.

Under typical United States laundry use (where the detergent is usually free of oxidative bleaches and enzymes for stain removal), it is common practice to use a product containing oxidants (typically sodium perborate or sodium percarbonate) and enzymes (proteolytic and amylolytic) in addition to the detergent to improve performance. These oxidant-containing products are usually formulated to deliver about 25–50 ppm A.O. (hydrogen peroxide) at a product use concentration of about 0.17% solution in the washing machine. When the inventive perhydrolysis system is intended for use with detergent in wash water at temperatures from about 70° F. to about 100° F., then a preferred formulation preferably has the source of hydrogen peroxide, the substrate, and the modified enzyme in a weight ratio between about 2400:200:1 and 48:20:1. A particularly preferred enzymatic perhydrolysis system of the invention has a weight ratio of sodium perborate tetrahydrate, trioctanoin and modified enzyme 1 in a weight ratio of 95:39:1. Such laundry additive formulations generate about 25–50 ppm A.O. (hydrogen peroxide), 2–20 ppm A.O. (theoretical peracid) and 0.1 ppm to 10 ppm enzyme in the wash solution at a product use concentration of about 0.17%.

Example 25 illustrates how specific designated base pair changes were made in the Lipase 1 gene from ATCC 53552 to obtain modified enzymes of the invention.

EXAMPLE 25

Specific designated base pair changes were made in the Lipase 1 gene from ATCC 53552 by the method as described by Carter, *Biochem. J.*, 237, pp. 1–7 (1986). The Eco RI-Sph I fragment from PSN tac II containing the entire Lipase 1 gene plus the tac II promotor was ligated into an M13 MP 18 vector which had been digested with Eco RI and Sph I. DNA sense strands were prepared and used as mutagenesis templates. A synthetic primer containing the desired mutation coding for the amino acid change was annealed to the single stranded template creating a double stranded region with one or more base pair mismatches. Nucleotides and the necessary enzymes were added in order to create double stranded plasmid from the primer and template. The resulting plasmid was transformed into *E. coli* JM101 and colonies were analyzed for the desired nucleotide changes that result in an amino acid change. For example, mutants having amino acid replacements at position 126 (with Ala or Tyr) and position 206 (with Gln) were created by this site-directed mutagenesis method.

Specific designated base pair changes were also made in the Lipase 1 gene that did not result in an amino acid change, but rather created unique endonuclear restriction sites. The method used was as described by Norris et al., *Nucleic Acids Res.*, 11, pp. 5103–5112 (1983) and Wells et al., *Gene*, 34, pp. 315–323 (1985).

Site directed mutagenesis was done in order to create two sets of unique sites on either side of the active serine 126. These changes, which did not affect the amino acid sequence, were AatII-Bam HI. Similarly, unique Bst XI-Bam HI sites were created around the active His 206 site. Each of these sets of mutations was done individually, thus creating two different plasmids with unique sites into which a piece of synthetic DNA or cassette carrying the desired amino acid change(s) can be ligated (and exchanged for the wild type Lipase 1 gene). Specifc base changes were as follows:

Aat II: CACTTC to GACGTC
Bam HI: GGCTCG to GGATCC
BST XI: CCGGTGTTCTGG to CCAGTGTTCTGG
BAG HI: GGTAGC to GGATCC

In order for the mutagenized Bst XI site to be unique for the His 206 cassettes, a Bst XI site at serine 126 had to be eliminated by changing the serine 126 codon from TCC to TCG.

The plasmid carrying the mutations for the serine cassettes is designated pGCtacII3AB, indicating a pBR322 plasmid carrying the tacII promoter and the lipase gene with the unique Aat II-Bam HI sites. The plasmid for the histidine mutants was designated pU-CI19tacII3BB, indicating a pUC plasmid carrying the tacII promoter and the lipase gene with the unique Bst XI-Bam HI sites.

All mutants with single amino acid changes other than those described above were done in this way. For the generations of random mutants, cassettes containing random base changes were used.

Double mutants were constructed by digesting the plasmid PGC tac II 3AB containing the desired mutation in the amino acid 126 region with Asp 718 and Acc I, and isolating the 300 base pair fragments. A plasmid PUC 119 tac II 3BB with the amino acid change in the 206 region was digested with the same restriction endonucleases and the 300 base pair fragment ligated into the resulting vector.

The enzymes with lipse activity were isolated as follows. Cells were grown for 20 h. at 37° C. in two tubes of 5ml LB +carbeniciuin (50 μg/ml). Cells were spun down at 6000 rev/min for 8 minutes at 4° C. in a Sorvall RC-5B. Each cell pellet was resuspended in 1 ml of cold 20% sucrose, 10 mM NaPi (filter sterilized), and 100 μL of 0.25M EDTA pH 8.0. The suspension was incubated on ice for 10–15 minutes, and then centrifuged at 6000 rev/min for six minutes at 4° C. The supernatant was then assayed for hydrolytic and perhydrolytic activity.

Purification was generally as follows. Fermentation broth was centrifuged at four thousand g for twenty minutes. The supernatant was decanted, and the cell paste frozen to minus seventy degrees centigrade. The cell paste was then thawed, and homogenized in a Waring blender with four volumes of a buffer consisting of 20% sucrose, 10 mM sodium-phosphate, pH 8. After thirty minutes of stirring, polyethyleninimine was added to a final concentration of 0.1% and stirred an additional five minutes. The slurry was then centrifuged at four thousand g for twenty minutes. The supernatant was filtered though a 0.22 micron filter; 10 mM sodium-phosphate, pH 8 was added to the supernatant until the conductivity was 2.2 milliohms. The resulting preparation was chromatographed on a sulfoyl-propyl cation exchange resin using 10 mM sodium-phosphate, pH 8. The lipase enzyme was eluted from the resin using 250 mM sodium chloride, 10 mM sodium phosphate, pH 8. At this point, the preparation is greater than ninety-five percent pure, as judged by SDS-PAGE.

The screening method used for detecting better perhydrolase mutants expressed by the *E. coli* was as follows. Transformants containing mutagenized DNA were streaked onto 1.2 micron cellulose acetate filters on Luria Agar (LA) +50 μg/ml Carbenicillin plates to obtain approximately 500 colonies per plate (150 mm petri dishes). Wild type controls were dot inoculated on a small area of each plate and the plates were incubated for 20 hrs. at 37° C.

The cellulose acetate filters containing the transformants and wild type controls were then lifted and transferred to fresh LA +Carb plates and stored at 4° C. The plates from which the filters were lifted were screened for lipase perhydrolysis activity by pouring 18 mls. per plate of an agarose overlay containing:

0.8% agarose in 0.4M $NaH_2PO_4$, pH 9.5
0.1% Trioctanoin/0.01% SDS
500 ppm $H_2O_2$
1 mg/ml o-tolidine.

Positive colonies (indicating perhydrolysis) produced a dark yellow color after 2 hrs. of incubation at room temperature and were selected for by comparison with the wild type controls.

Each corresponding positive colony was picked from the original filter and inoculated into a well of a 96-well sterile titertek plate containing 100 μl of LB +50 μg/ml Carbenicillin (one column was inoculated with a wild type control). This plate was grown 6–7 hrs. (or overnight). Using a 96-pronged plate stamper, an LA+Carb plate with a cellulose acetate filter and allowed to grow for 20 hrs. at 37° C. This plate was then rescreened using the overlay procedure described above for selection of the best mutants. Single glycerol stocks were then prepared by picking colonies from the stamped filter and growing in 5 mls. LB 6-7 hrs at 37° C. These glycerol stocks are used for larger scale testing.

From the procedures of preparing and screening described above, a number of modified enzymes having comparable or improved peracid production with respect to the reference enzyme were isolated from *E. coli* colonies with mutant Lipase genes. Table 11 summarizes such modified enzymes of the invention.

TABLE 11

| Enzyme | (μg/ml) | Acid (meq × 10³) | Peracid (meq × 10³), (ppm) | | Ratio A/P |
|---|---|---|---|---|---|
| Wild Type | (0.4) | 17 | 3.7 | 3.9 | 5 |
|  | (0.8) | 26 | 6.2 | 6.6 | 4 |
|  | (1.5) | 51 | 9.4 | 9.8 | 5 |
| Gln-205 | (0.3) | 9.7 | 2.8 | 3.0 | 3 |
| Gln-205 | (0.6) | 11 | 3.9 | 4.2 | 3 |
| Thr-207 | (0.9) | 21 | 4.5 | 4.8 | 5 |
| Pro-205 | (1.5) | 22 | 6.4 | 6.8 | 4 |
| Lys-205 | (2.4) | 25 | 4.8 | 5.1 | 3 |
| Ser-127 | (20) | 5.1 | 1.3 | 4.1 | 4 |
| Gly-207 | (2.3) | 6 | 1.4 | 1.5 | 4 |
| Trp-207 | (0.9) | 25 | 5.6 | 5.9 | 4 |
| Lys-207 | (0.3) | 20 | 6.7 | 7.1 | 3 |
| Asn-205 | (0.3) | 12 | 5.3 | 5.6 | 2 |
| Asn-205 | (0.64) | 14 | 8.7 | 9.3 | 2 |
| Asn-205/ Thr-207 | (0.3) | 19 | 7.4 | 7.5 | 3 |
| Glu-205 | (0.4) | 18 | 3.9 | 4.1 | 5 |
| Cys-205 | (0.50) | 19 | 5.8 | 6.2 | 3 |
| Arg-127/ Thr-207 | (30) | 23 | 13 | 13.4 | 2 |
| Asn-127/ Gln-205 | (30) | 9.7 | 4.3 | 4.6 | 2 |
| Ser-127/ Thr-207 | (19) | 19 | 7.9 | 8.4 | 2 |
| Ser-127/ Asn-205 | (8) | 13 | 5.5 | 5.8 | 2 |
| Ser-127/ Thr-205 | (25) | 9.4 | 7.1 | 7.6 | 1 |
| Arg-127/ Asn-205 | (12) | 16 | 9.5 | 1.01 | 2 |
| Thr-127/ Gln-205 | (50) | 20 | 16 | 16.8 | 1 |
| Asn-127/ Thr-207 | (44) | 18 | 14 | 14.7 | 1 |
| Thr-127/ Asn-205 | (20) | 14 | 6.8 | 7.2 | 1 |
| Arg-127 | (2.6) | 14 | 2.8 | 3.0 | 4 |
| Ala-207 | (0.2) | 13 | 2.9 | 3.1 | 4 |
| Arg-127/ Ala-207 | (17) | 12 | 9 | 9 | 1 |
| Ala-207 | (0.2) | 13 | 2.9 | 3.1 | 5 |
| Thr-127/ Ala-207 | (14) | 8.6 | 2.4 | 2.6 | 4 |
| Thr-127/ Ala-207 | (22) | 9.7 | 6.3 | 6.7 | 2 |

The assay condition for determining the ratio of acid to peracid were as follows.
 substrate 0.4% tricaprylin
 emulsifier 0.04% sodium dodecylsufate
 $H_2O_2$ 800 ppm A.O.
 50 μM EDTA
 reaction pH 10.0
 reaction temperature RT
 reaction time 14 minutes The pH-stat monitors both hydrolysis of tricaprylin to produce caprylic acid and perhydrolysis of tricaprylin to produce peroctanoic acid. Both acid products are titrated by pH stat, as the pka of peroctanoic acid =8.5 and the caprylic (octanoic) acid 3.5. The data is acquired off the instrument as total meq product/14 minutes. Peroctanoic acid is quantitatively assayed, after decomposition of $H_2O_2$ by addition of catalase, on a Brinkman Autotitrator by addition of excess acidified potassium iodide and titration with dilute thiosulfate. It is believed that the EDTA stabilizes the peroctanoic acid by reducing metal-catalyzed decomposition. The peracid titration yields meq peracid which is substracted from the total acid observed by pH-stat, to yield a net hydrolysis (acid) value.

As may be seen from the data of Table 11, a number of modified enzymes with comparable or considerably better efficiency with respect to the reference enzyme have been made.

While the invention has been described in connection with specific embodiments thereof, it will be understood that it is capable of further modifications, and this application is intended to cover any variations, uses or adaptations of the invention following, in general, the principles of the invention and including such departures from the disclosure as come within the known or customary practice in the art to which the invention pertains and as may be applied to the essential features hereinbefore set forth, and as fall within the scope of the invention and the limits of the appended claims.

It is claimed:

1. An enzymatic perhydrolysis composition for in situ generation of peracid comprising:
 (a) a modified enzyme having substantially the amino acid sequence 1                                          10
ala pro leu pro asp thr pro gly ala pro phe pro 20
ala val ala asn phe asp arg ser gly pro tyr thr 30
the ser ser gln ser glu gly pro ser cys arg ile 40
tyr arg pro arg asp leu gly gln gly gly val arg 50                                60
his pro val ile leu trp gly asn gly thr gly ala 70
gly pro ser thr tyr ala gly leu leu ser his trp 80
ala ser his gly phe val val ala ala ala glu thr 90
ser asn ala gly thr gly arg glu met leu ala cys 100
leu asp tyr leu val arg glu asn asp thr pro tyr 110                              120
gly thr tyr ser gly lys leu asn thr gly arg val 130
gly thr ser gly his ser gln gly gly gly gly ser 140
ile met ala gly gln asp thr arg val arg thr thr 150
ala pro ile gln pro tyr thr leu gly leu gly his 160
asp ser ala ser gln arg arg gln gln gly pro met 170                                  180
phe leu met ser gly gly gly asp thr ile ala phe 190
pro tyr leu asn ala gln pro val tyr arg arg ala 200
asn val pro val phe trp gly glu arg arg tyr val 210
ser his phe glu pro val gly ser gly gly ala tyr -continued

```
                    220
arg gly pro ser thr ala trp phe arg phe gln leu 230                              240
met asp asp gln asp ala arg ala thr phe tyr gly 250
ala gln cys ser leu cys thr ser leu leu trp ser val glu arg arg gly leu 1                            10
ala pro leu pro asp thr pro gly ala pro phe pro 20
ala val ala asn phe asp arg ser gly pro tyr thr 30
thr ser ser gln ser glu gly pro ser cys arg ile 40
tyr arg pro arg asp leu gly gln gly gly val arg 50                              60
his pro val ile leu trp gly asn gly thr gly ala 70
gly pro ser thr tyr ala gly leu leu ser his trp 80
ala ser his gly phe val val ala ala ala glu thr 90
ser asn ala gly thr gly arg glu met leu ala cys 100
leu asp tyr leu val arg glu asn asp thr pro tyr 110                             120
gly thr tyr ser gly lys leu asn thr gly arg val 130
gly thr ser gly his ser gln gly gly gly gly ser 140
ile met ala gly gln asp thr arg val arg thr thr 150
ala pro ile gln pro tyr thr leu gly leu gly his 160
asp ser ala ser gln arg arg gln gln gly pro met 170                             180
phe leu met ser gly gly gly asp thr ile ala phe 190
pro tyr leu asn ala gln pro val tyr arg arg ala 200
asn val pro val phe trp gly glu arg arg tyr val 210
ser his phe glu pro val gly ser gly gly ala tyr 220
arg gly pro ser thr ala trp phe arg phe gln leu 230                             240
met asp asp gln asp ala arg ala thr phe tyr gly 250
ala gln cys ser leu cys thr ser leu leu trp ser val glu arg arg gly leu
``` but modified therefrom by differing by at least one amino acid within about six amino acids on either side of serine 126, asparagine 176, or histidine 206 in the primary sequence;

(b) a substrate being capable of hydrolysis by the modified enzyme of (a), the substrate including a glyceride, an ethylene glycol derivative or a propylene glycol derivative, the glyceride being one or more of a monoglyceride with a fatty acid chain of one to about twelve carbons, a diglyceride with fatty acid chains of one to about twelve carbons, and a triglyceride with fatty acid chains of one to about twelve carbons, the ethylene glycol derivative having the structure

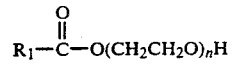

where n=1-10 and where

is the acyl moiety of a fatty acid and $R_1$ has one to about twelve carbons, and the propylene glycol derivative having the structure

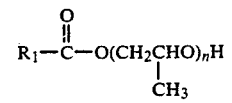

where n and $R_1$ are defined above; and (c) a source of peroxygen which will react with (a) and (b) to produce peracid in the presence of a substrate-solubilizing aqueous solution.

2. The enzymatic perhydrolysis composition of claim 1 wherein the substrate is a monoglyceride with a fatty acid chain $R_1$, a diglyceride with fatty acid chains $R_1$ and $R_2$, or a triglyceride with fatty acid chains $R_1$, $R_2$ and $R_3$, and wherein $R_1=C_6-C_{10}$, $R_2=C_6-C_{10}$ and $R_3=C_6-C_{10}$.

3. The enzymatic perhydrolysis composition of claim 1 wherein the substrate-solubilizing aqueous solution includes an emulsifying agent.

4. The enzymatic perhydrolysis composition of claim 3 wherein the emulsifier includes: a water soluble polymer; a cationic, nonionic, anionic, amphoteric or zwitterionic surfactant; bile salts; or mixtures of any of the foregoing.

5. The enzymatic perhydrolysis composition of claim 3 further comprising a buffer, the buffer including a carbonate, phosphate, silicate, borate, or hydroxide.

6. The enzymatic perhydrolysis composition of claim 1 wherein the modified enzyme has glutamine at position 205, asparagine at position 205, asparagine at position 205 and threonine at position 207, serine at position 127 and asparagine at position 205, serine at position 127 and threonine at position 205, threonine at position 127 and glutamine at position 205, asparagine at position 127 and threonine at position 207, threonine at position 127 and asparagine at position 205, or arginine at position 127 and alanine at position 207.

7. The enzymatic perhydrolysis composition of claim 6 wherein the substrate is trioctanoin or tridecanoin.

8. The enzymatic perhydrolysis composition of claim 6 wherein the substrate includes at least one glyceride moiety.

9. The enzymatic perhydrolysis composition of claim 8 wherein the glyceride substrate is selected from the group consisting of diglycerides and triglycerides.

10. A process for bleaching materials, comprising the steps of contacting the materials with an aqueous solution and combining with the aqueous solution an enzymatic perhydrolysis composition for in situ generation of peracid, including:

(a) a modified enzyme having substantially the amino acid sequence

```
  1                                    10
ala pro leu pro asp thr pro gly ala pro phe pro 20
ala val ala asn phe asp arg ser gly pro tyr thr 30
thr ser ser gln ser glu gly pro ser cys arg ile 40
tyr arg pro arg asp leu gly gln gly gly val arg 50                                   60
his pro val ile leu trp gly asn gly thr gly ala 70
gly pro ser thr tyr ala gly leu leu ser his trp 80
ala ser his gly phe val val ala ala ala glu thr 90
ser asn ala gly thr gly arg glu met leu ala cys 100
leu asp tyr leu val arg glu asn asp thr pro tyr 110                                   120
gly thr tyr ser gly lys leu asn thr gly arg val 130
gly thr ser gly his ser gln gly gly gly gly ser 140
ile met ala gly gln asp thr arg val arg thr thr 150
ala pro ile gln pro tyr thr leu gly leu gly his 160
asp ser ala ser gln arg arg gln gln gly pro met 170                                   180
phe leu met ser gly gly gly asp thr ile ala phe 190
pro tyr leu asn ala gln pro val tyr arg arg ala 200
asn val pro val phe trp gly glu arg arg tyr val 210
ser his phe glu pro val gly ser gly gly ala tyr 220
arg gly pro ser thr ala trp phe arg phe gln leu 230                                   240
met asp asp gln asp ala arg ala thr phe tyr gly 250
ala gln cys ser leu cys thr ser leu leu trp ser val glu arg arg gly leu
``` but modified therefrom by differing by at least one amino acid within about six amino acids on either side of serine 126, asparagine 176, or histidine 206 in the primary sequence;

(b) a substrate being capable of hydrolysis by the modified enzyme of (a), the substrate including a glyceride, an ethylene glycol derivative or a propylene glycol derivative, the glyceride being one or more of a monoglyceride with a fatty acid chain of one to about twelve carbons, a diglyceride with fatty acid chains of one to about twelve carbons, and a triglyceride with fatty acid chains of one to about twelve carbons, the ethylene glycole derivative having the structure

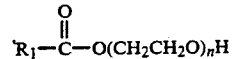

where n=1-10 and where

is the acyl moiety of a fatty acid and $R_1$ has one to about twelve carbons, and the propylene glycol derivative having the structure
where n and $R_1$ are defined above; and (c) a source of peroxygen which will react with (a) and (b) to produce peracid in the presence of a substrate-solubilizing aqueous solution.

11. The process of claim 10 wherein the substrate is a monoglyceride with a fatty acid chain $R_1$, a diglyceride with fatty acid chains $R_1$ and $R_2$, or a triglyceride with fatty acid chains $R_1$, $R_2$ and $R_3$, and wherein $R_1=C_6-C_{10}$, $R_2=C_{66}-C_{10}$ and $R_3=C_{66}-C_{10}$.

12. The process of claim 10 wherein the composition further comprises an emulsifying agent, and wherein the modified enzyme has glutamine at position 205, asparagine at position 205, asparagine at position 205 and threonine at position 207, serine at position 127 and asparagine at position 205, serine at position 127 and threonine at position 205, threonine at position 127 and glutamine at position 205, asparagine at position 127 and threonine at position 207, threonine at position 127 and asparagine at position 205, or arginine at position 127 and alanine at position 207.

13. The process of claim 12 wherein the emulsifier is selected from the group consisting of: water soluble polymers; cationic, nonionic, anionic, amphoteric and zwitterionic surfactants; bile salts; and mixtures of any of the foregoing.

14. The process of claim 10 further comprising a buffer selected from the group consisting of carbonates, phosphates, silicates, borates and hydroxides.

15. The process of claim 10 further comprising an emulsifier which is capable of at least maintaining or improving peracid yields achieved by the composition in the absence of the emulsifier.

* * * * *

UNITED STATES PATENT AND TRADEMARK OFFICE
CERTIFICATE OF CORRECTION

PATENT NO. : 5,108,457

DATED : April 28, 1992

INVENTOR(S) : Ayrookaram J. Poulose, Susan A. Anderson

It is certified that error appears in the above-identified patent and that said Letters Patent is hereby corrected as shown below:

Column 30, line 34, in Claim 1    delete "the"
    insert---thr---

Column 31, line 13, in Claim 1    delete lines 13 through 58

Column 33, line 13 in Claim 10    delete "the"
    insert---thr---

Column 34, line 26 in Claim 10    insert---

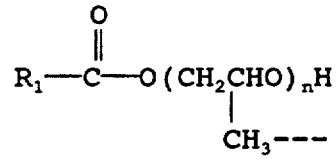

after "structure"

Signed and Sealed this

Nineteenth Day of October, 1993

Attest:

BRUCE LEHMAN

Attesting Officer    Commissioner of Patents and Trademarks